United States Patent
Scritchfield et al.

(10) Patent No.: US 10,702,707 B2
(45) Date of Patent: Jul. 7, 2020

(54) HAND SANITIZER STATION

(71) Applicant: CP Studios LLC, Salt Lake City, UT (US)

(72) Inventors: George Scritchfield, Pleasant Hill, CA (US); Nigel Waites, Lakeville, MN (US)

(73) Assignee: CP Studios LLC, Salt Lake City, UT (US)

( * ) Notice: Subject to any disclaimer, the term of this patent is extended or adjusted under 35 U.S.C. 154(b) by 914 days.

(21) Appl. No.: 14/815,993

(22) Filed: Aug. 1, 2015

(65) Prior Publication Data

US 2016/0030766 A1    Feb. 4, 2016

Related U.S. Application Data

(60) Provisional application No. 62/032,050, filed on Aug. 1, 2014, provisional application No. 62/033,144, filed on Aug. 5, 2014.

(51) Int. Cl.
| | |
|---|---|
| *A61N 5/06* | (2006.01) |
| *G06F 3/01* | (2006.01) |
| *G06K 9/00* | (2006.01) |

(52) U.S. Cl.
CPC ............ *A61N 5/0624* (2013.01); *G06F 3/011* (2013.01); *G06K 9/00228* (2013.01);
(Continued)

(58) Field of Classification Search
CPC ...... A61N 5/06; A61N 5/0613; A61N 5/0616; A61N 5/0624; A61N 2005/0627; A61N 2005/0628; A61N 2005/0635; A61N 2005/0643; A61N 2005/0661; G06K 9/00221; G06K 9/00228; G06K 9/00248; G06K 9/00261; G06K 9/00268; G06K 9/00275; G06K 9/00281; G06K 9/00288;
(Continued)

(56) References Cited

U.S. PATENT DOCUMENTS

| | | | |
|---|---|---|---|
| 8,884,258 B1 * | 11/2014 | Liao .......................... | A61L 2/10 |
| | | | 250/504 H |
| 9,438,869 B2 * | 9/2016 | Gillies ................... | A61B 5/055 |

(Continued)

OTHER PUBLICATIONS

International Search Report and Written Opinion for PCT Application No. PCT/US15/43344, dated Jan. 15, 2016, 12 pages.

*Primary Examiner* — Ahmed M Farah
(74) *Attorney, Agent, or Firm* — Patent Law Works LLP

(57) ABSTRACT

A system and method for detecting, using a sensor, an initiation event; capturing, using a camera, an image of a user's face responsive to the initiation event; activating, responsive to facial recognition and a determination based on one of exposure data associated with the user and the absence thereof that the user has not exceed a safe use standard for ultraviolet light, an ultraviolet source; the ultraviolet source and an activation duration sufficient to sanitize a surface located within a compartment. In one embodiment, visually presenting, by a display, a plurality of graphic elements associated with a plurality of potential content for presentation to the user; and presenting user selected content to the user when the ultraviolet source is activated and responsive to determining a user's selection, wherein the user's selection is made touch-lessly.

18 Claims, 9 Drawing Sheets

(52) U.S. Cl.
CPC .. *G06K 9/00375* (2013.01); *A61N 2005/0627* (2013.01); *A61N 2005/0643* (2013.01); *A61N 2005/0661* (2013.01)

(58) Field of Classification Search
CPC ........... G06K 9/00295; G06K 9/00302; G06K 9/00335; G06K 9/00355; G06K 9/00362; G06K 9/00375; G06K 9/00395; G06F 3/01; G06F 3/011; G06F 3/012; G06F 3/013; G06F 3/018
USPC ......... 607/88–91, 93, 94; 382/115, 117, 118; 422/22, 24, 28
See application file for complete search history.

(56) References Cited

U.S. PATENT DOCUMENTS

| | | | |
|---|---|---|---|
| 9,934,427 B2* | 4/2018 | Derenne | G06F 16/78 |
| 2007/0222554 A1* | 9/2007 | Hart | G07C 9/00071 |
| | | | 340/5.6 |
| 2010/0266446 A1 | 10/2010 | Constantacos | |
| 2012/0075464 A1* | 3/2012 | Derenne | A61B 5/0013 |
| | | | 348/135 |
| 2012/0156094 A1 | 6/2012 | Gordon | |
| 2012/0187146 A1 | 7/2012 | Chopra | |
| 2014/0015951 A1 | 1/2014 | Millikan | |
| 2014/0244344 A1* | 8/2014 | Bilet | G06Q 10/0635 |
| | | | 705/7.28 |
| 2014/0330579 A1* | 11/2014 | Cashman | E04H 1/1222 |
| | | | 705/2 |
| 2016/0000951 A1* | 1/2016 | Kreiner | A61L 2/0047 |
| | | | 422/24 |
| 2017/0213079 A1* | 7/2017 | Herger | G06T 7/0012 |
| 2017/0364091 A1* | 12/2017 | Bennett | G06F 21/602 |
| 2018/0357886 A1* | 12/2018 | Tavori | G08B 21/245 |

* cited by examiner

HAND SANITIZER STATION

CROSS-REFERENCE TO RELATED APPLICATIONS

The present application claims priority to U.S. Provisional Application No. 62/032,050 entitled "Ultraviolet Hand Sanitizer with Advertising and Promotion Presentation" and filed Aug. 1, 2014, and U.S. Provisional Application No. 62/033,144 entitled "Ultraviolet Hand Sanitizer with Facial Recognition" and filed Aug. 5, 2014, the contents of each of which are hereby incorporated by references in their entireties.

BACKGROUND

The present disclosure relates to the field of hand sanitizers. More particularly, the present disclosure relates to hands-free selection of content presented by a hand sanitizer station as well as limiting the use of an ultraviolet (UV) hand sanitizer to prevent excessive exposure to a single user.

Hand sanitizer stations are used to sanitize the hands of an individual. Some hand sanitizers expose a user's hands to ultraviolet (UV) light in order to sanitize the hands. However, present hand sanitizers fail to provide a system or method for preventing a particular user from over exposing themselves to UV light, for example, by frequent, repeated use in a period of time. Hand sanitizer stations also fail to provide user-selectable content for presentation to a user while the hand sanitation occurs. Furthermore, hand sanitizer stations further fail to provide a touchless system or method for a user to select the user-selectable content for presentation to the user during hand sanitation.

SUMMARY

According to one innovative aspect of the subject matter described in this disclosure, a sensor configured to detect an initiation event; a camera configured to capture an image of a user's face responsive to the initiation event, the camera communicatively coupled to the sensor; and an ultraviolet source configured to activate responsive to facial recognition and a determination based on one of exposure data associated with the user and the absence thereof that the user has not exceed a safe use standard for ultraviolet light; the ultraviolet source and an activation duration sufficient to sanitize a surface located within a compartment.

In general, another innovative aspect of the subject matter described in this disclosure may be embodied in methods that include detecting, using a sensor, an initiation event; capturing, using a camera, an image of a user's face responsive to the initiation event; and activating, responsive to facial recognition and a determination based on one of exposure data associated with the user and the absence thereof that the user has not exceed a safe use standard for ultraviolet light, an ultraviolet source; the ultraviolet source and an activation duration sufficient to sanitize a surface located within a compartment.

Other aspects include corresponding methods, systems, apparatus, and computer program products. These and other implementations may each optionally include one or more of the following features. For instance, the operations further include: visually presenting, by a display, a plurality of graphic elements associated with a plurality of potential content for presentation to the user; and presenting user selected content to the user when the ultraviolet source is activated and responsive to determining a user's selection, wherein the user's selection is made touch-lessly. For instance, the operations further include: presenting supplemental information to the user after a conclusion of the content presented to the user when the ultraviolet source is activated. For instance, the operations further include: detecting, by one or more micro-sonars, the user's movement in proximity to the display touch-lessly and visually distinguishing a graphic element associated with content based on the user's movements, the visually distinguished graphic element determined to be selected responsive to detecting the initiation event. For instance, the operations further include: cycling through the potential content for presentation to the user while the ultraviolet source is activated and visually distinguishing a different graphic element associated with potential content for presentation to the user while the ultraviolet source is activated at an interval, the visually distinguished graphic element determined to be selected responsive to detecting the initiation event.

For instance, the features include: the content presented to the user has a duration similar to the activation duration; the initiation event includes the presence of one or more of an object and a user's hand located within the compartment; the user's selection is determined responsive to the sensor detecting the initiation event; the ultraviolet source is activated responsive to the user passing a screening and responsive to the facial recognition and determination based on one of the exposure data associated with the user and the absence thereof that the user has not exceed the safe use standard for ultraviolet light and the ultraviolet source remains inactive otherwise; the screening is based on one or more of a user's height and whether the user's facial features are determined to be similar to those of a child.

It should be understood that the above is not all-inclusive and many additional steps, features and advantages are contemplated and fall within the scope of the present disclosure. Moreover, it should be understood that the language used in the present disclosure has been principally selected for readability and instructional purposes, and not to limit the scope of the subject matter disclosed herein.

BRIEF DESCRIPTION OF THE DRAWINGS

The disclosure is illustrated by way of example, and not by way of limitation in the figures of the accompanying drawings in which like reference numerals are used to refer to similar elements.

DETAILED DESCRIPTION

Figure 1:
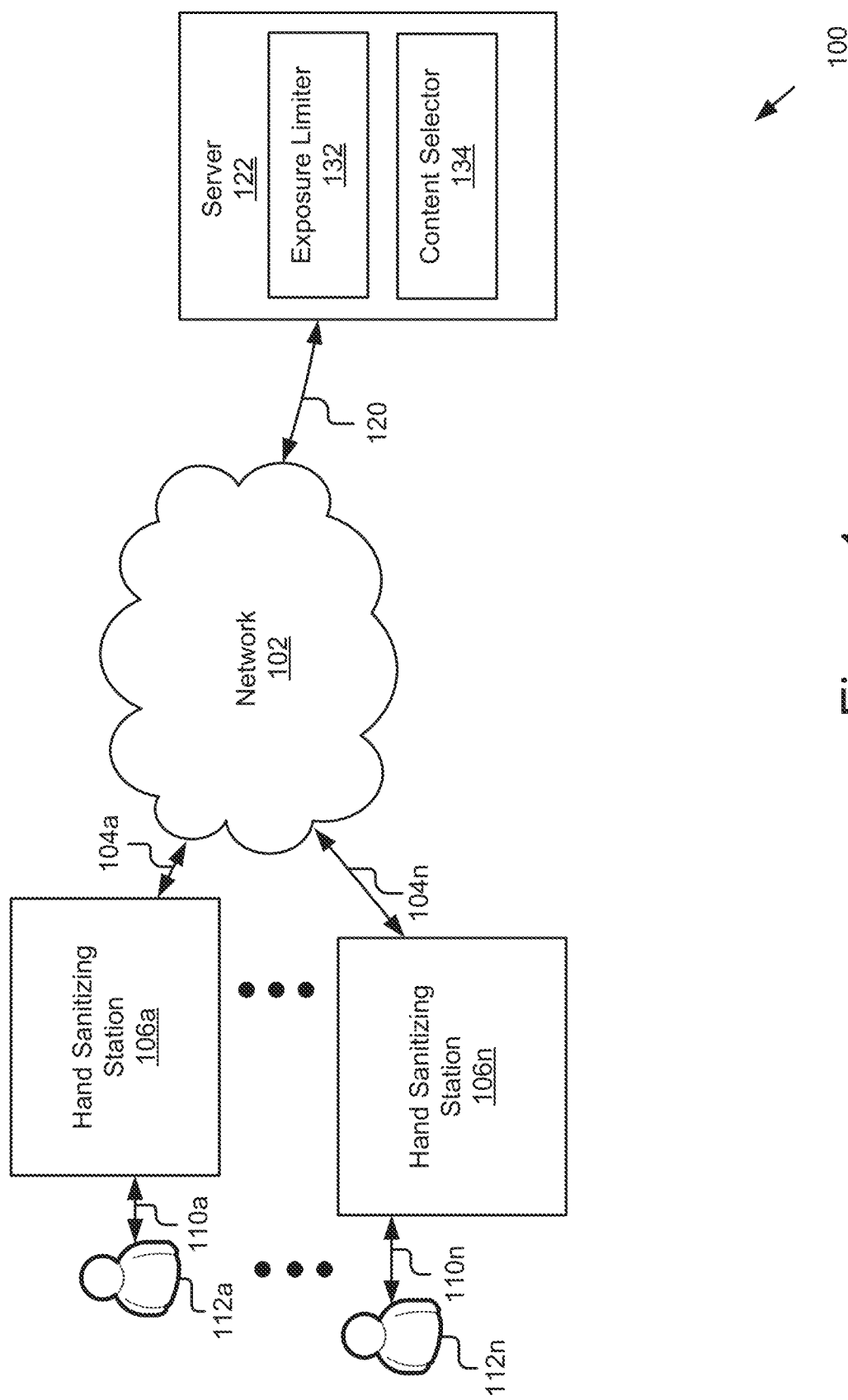
FIG. 1 is block diagram of a system for one or more of UV exposure limitation for hand sanitation and touchless selection of content for presentation on a hand sanitizer station according to one embodiment.

FIG. 1 is block diagram of a system for one or more of UV exposure limitation for hand sanitation and touchless selection of content for presentation on a hand sanitizer station according to one embodiment. The illustrated system 100 includes hand sanitizing stations 106a ... 106n, and a server 122, which are communicatively coupled via a network 102 for interaction with one another. For example, the hand sanitizing stations 106a ... 106n may be respectively coupled to the network 102 via signal lines 104a ... 104n and may be accessed by users 112a ... 112n (also referred to individually and collectively as 112) as illustrated by lines 110a ... 110n. The server 122 may be coupled to the network 102 via signal line 120. The use of the nomenclature "a" and "n" in the reference numbers indicates that any number of those elements having that nomenclature may be included in the system 100.

The network 102 may include any number of networks and/or network types. For example, the network 102 may include, but is not limited to, one or more local area networks (LANs), wide area networks (WANs) (e.g., the Internet), virtual private networks (VPNs), mobile (cellular) networks, wireless wide area network (WWANs), Wi-Fi networks, WiMAX® networks, Bluetooth® communication networks, peer-to-peer networks, other interconnected data paths across which multiple devices may communicate, various combinations thereof, etc. Data transmitted by the network 102 may include packetized data (e.g., Internet Protocol (IP) data packets) that is routed to designated computing devices coupled to the network 102. In some implementations, the network 102 may include a combination of wired and wireless (e.g., terrestrial or satellite-based transceivers) networking software and/or hardware that interconnects the computing devices of the system 100. For example, the network 102 may include packet-switching devices that route the data packets to the various computing devices based on information included in a header of the data packets.

The data exchanged over the network 102 can be represented using technologies and/or formats including the hypertext markup language (HTML), the extensible markup language (XML), JavaScript Object Notation (JSON), Comma Separated Values (CSV), etc. In addition, all or some of links can be encrypted using conventional encryption technologies, for example, the secure sockets layer (SSL), Secure HTTP (HTTPS) and/or virtual private networks (VPNs) or Internet Protocol security (IPsec). In another embodiment, the entities can use custom and/or dedicated data communications technologies instead of, or in addition to, the ones described above. Depending upon the embodiment, the network 102 can also include links to other networks.

The hand sanitizer stations 106a ... 106n (also referred to individually and collectively as 106) are computing devices having UV sanitation, data processing and communication capabilities. While FIG. 1 illustrates two hand sanitizing stations 106, the present specification applies to any system architecture having one or more hand sanitizing stations. The components of an embodiment of a hand sanitizer station 106 are described below with reference to FIGS. 2A-B. In one embodiment, the hand sanitizer stations 106a ... 106n may couple to and communicate with one another and the other entities of the system 100 via the network 102 using a wireless and/or wired connection.

The server 122 may include one or more computing devices having data processing, storing, and communication capabilities. For example, server 122 may include one or more hardware servers, server arrays, storage devices, systems, etc., and/or may be centralized or distributed/cloud-based. In some implementations, server 122 may include one or more virtual servers, which operate in a host server environment and access the physical hardware of the host server including, for example, a processor, memory, storage, network interfaces, etc., via an abstraction layer (e.g., a virtual machine manager).

In one embodiment, the server 122 includes a content server. For example, in one embodiment, the system 100 includes a server 122 that is a content server and the content server provides content for display on one or more hand sanitizing stations. Examples of content may include one or more of user created content, news, advertisements, health information, weather, sales, promotions, facts, songs, video or any other information. For example, in one embodiment, the server 122 is a content server and pushes content (e.g. advertisements) to a hand sanitizer station 106. In one embodiment, the hand sanitizer's internal computing device contains a cache, so the content is only pushed once and then stored on the device reducing the bandwidth required for the network. It will be recognized that the preceding are merely examples of providing content and types of content and that other examples exist.

The server 122, as depicted, may include the exposure limiter 132 or a portion thereof according to one embodiment. For example, depending on the embodiment, the exposure limiter 132 and its functionality may not be performed entirely by the server 122 and a portion, or the entirety, of the exposure limiter 132 may be included in and/or performed by a hand sanitizer station 106.

The server 122, as depicted, may include the content selector 134 or a portion thereof according to one embodiment. For example, depending on the embodiment, the content selector 134 and its functionality may not be performed entirely by the server 122 and a portion, or the entirety, of the exposure limiter 134 may be included in and/or performed by a hand sanitizer station 106.

It should be understood that the system 100 illustrated in FIG. 1 is representative of an example system for one or more of UV exposure limitation for hand sanitation and touchless selection of content for presentation on a hand sanitizer station according to one embodiment, and that a variety of different system environments and configurations are contemplated and are within the scope of the present disclosure. For instance, various functionality may be moved from a server 122 to a hand sanitizing station 106, or vice versa and some implementations may include additional or fewer computing devices, services, and/or networks, and may implement various functionality client or server-side. Further, various entities of the system 100 may be integrated into to a single computing device or system or additional computing devices or systems, etc.

Figure 2A:
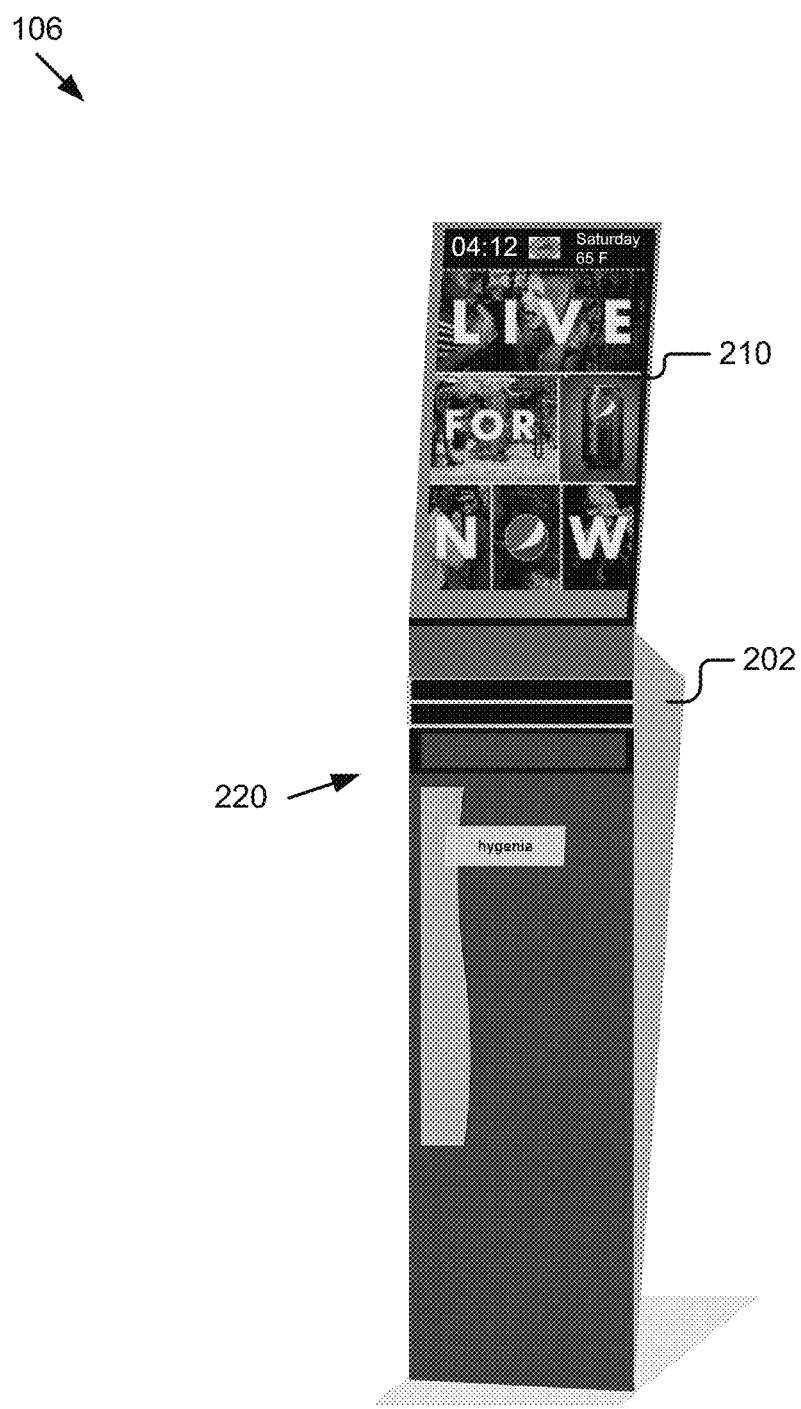
FIG. 2A is an illustration of an orthogonal view of an example hand sanitizer station according to one embodiment.

FIG. 2A is an illustration of an orthogonal view of an example hand sanitizer station 106 according to one embodiment. In one embodiment, the hand sanitizer station 106 uses UV light to sanitize a user's hands or other objects. Illustrated in FIG. 2A is one embodiment of an ultraviolet (UV) light hand sanitizer station 106. The components of a UV hand sanitizing station 106 are shown schematically in the block diagram of FIG. 2B discussed below. Preferably, the UV sanitizer station 106 is located within a public area such as a retail store, shopping area, restaurant, medical facility, etc.

Figure 2B:
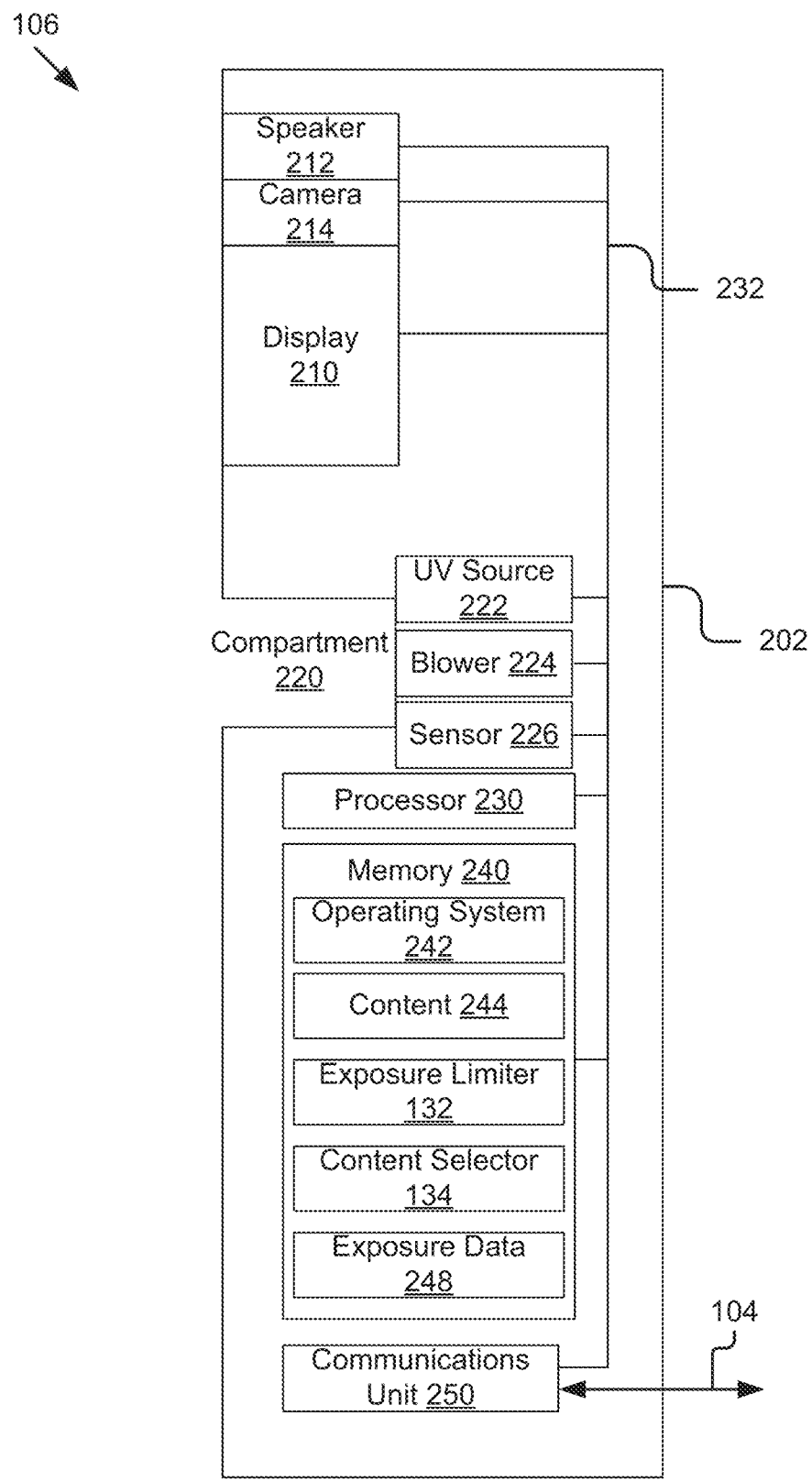
FIG. 2B is a block diagram illustrating an example schematic of a hand sanitizer station according to one embodiment.

Referring to FIG. 2B, in one embodiment, the hand sanitizer station 106 includes a stand or enclosure 202 that contains the various components of the hand sanitizer station 106. In the illustrated embodiment, the enclosure 200 contains a display 210 and a speaker 212 that are used to present audio-visual material to the users of the hand sanitizer station 106. In addition, the enclosure 200 includes one or more forward facing cameras 214 (e.g. a single camera, cameras in stereo, a plenoptic camera, etc.) that are able to capture images of users' faces that make use of the UV hand sanitizer station 106. In the illustrated embodiment, the enclosure 200 also includes an opening or compartment 220 that receives a user's hands or other items to be sanitized. In one embodiment, while the user's hands are in the compartment 220, the display 210 and/or speaker 214 will present content (e.g. an advertisement that is preferably related to the products that are available for sale in the retail store or shopping area in which the hand sanitizer station 106 is located) to the user.

The compartment or opening 220 is connected to a UV source 222, a blower 224, and one or more sensors 226. In one embodiment, the one or more sensors 226 include a sensor that detects the presence of hands or another object within the opening 220 and transmits this information to a processor 230 over a local bus or other communication channel 232. In one embodiment, the one or more sensors 226 includes a photodetector to detect one or more of when the UV source 222 turns on, how long the UV source is on and the intensity of the output of the UV source 222.

The processor 230 may execute code, routines and software instructions by performing various input/output, logical, and/or mathematical operations. The processor 202 may have various computing architectures to process data signals including, for example, a complex instruction set computer (CISC) architecture, a reduced instruction set computer (RISC) architecture, and/or an architecture implementing a combination of instruction sets. The processor 202 may be physical and/or virtual, and may include a single core or plurality of processing units and/or cores. In some implementations, the processor 230 may be coupled to the memory 240 via the bus 232 to access data and instructions therefrom and store data therein. The bus 232 may couple the processor 230 to the other components of the hand sanitizing station 106, for example, the memory 240, communication unit 250, the speaker 212, the camera 214, the display 210, the UV source 222, the blower, 224, and the one or more sensors 226. In some embodiments, the processor 230 may take the form of a general purpose CPU manufactured by Intel Corporation (Mountain View, Calif.) or Advanced Micro Devices, Inc. (Sunnyvale, Calif.), or pursuant to the specifications of ARM Holdings plc (Cambridge, England). In some embodiments the processor 230 may take the form of a special purpose processor (e.g. a application specific integrated circuit (ASIC) or a field programmable gate array (FPGA)).

The memory 240 may store and provide access to data to the other components of the hand sanitizing station 106. In some implementations, the memory 240 may store instructions and/or data that may be executed by the processor 230. For example, as depicted, the memory 240 may store the exposure limiter 132 or a portion thereof and/or the content selector 134 or a portion thereof. The memory 204 is also capable of storing other instructions and data, including, for example, an operating system, hardware drivers, other software applications, databases, etc. The memory 240 may be coupled to the bus 206 for communication with the processor 230 and the other components of the hand sanitizing station 106.

The memory 240 includes a non-transitory computer-usable (e.g., readable, writeable, etc.) medium, which can be any apparatus or device that can contain, store, communicate, propagate or transport instructions, data, computer programs, software, code, routines, etc., for processing by or in connection with the processor 230. In some implementations, the memory 240 may include one or more of volatile memory and non-volatile memory. For example, the memory 240 may include, but is not limited, to one or more of a dynamic random access memory (DRAM) device, a static random access memory (SRAM) device, a discrete memory device (e.g., a PROM, FPROM, ROM), a hard disk drive, an optical disk drive (CD, DVD, Blue-Ray™, etc.). It should be understood that the memory 240 may be a single device or may include multiple types of devices and configurations. In one embodiment, the memory 240 includes an operating system software 242, such as LINUX (available from multiple companies under open source licensing terms) or WINDOWS (available from Microsoft Corporation of Redmond, Wash.), as well as specific programming that controls the various operations of the UV sanitizer station 106 including the exposure limiter 132 and content selector 134 according to one embodiment.

In one embodiment, the sanitization process begins when the processor 230 turns on an ultraviolet (UV) light source 222 and a blower 224 for a predetermined amount of time. In one embodiment, the UV light source 222 emits a short wavelength UV light (e.g. UV-C in the range of 220 nm to 290 nm) that is designed to act as a surface germicide to kill or otherwise render harmless bacteria, viruses and other microorganisms found on the surface of the object within compartment 220. In the preferred embodiment, the UV light that falls on the object has been reflected off a reflective surface, such as aluminum, which has been shown to increase the germicidal effectiveness of UV light exposure. The duration of the exposure required to act as an effective germicide varies depending on the intensity of the light that falls on the object. While effective hand sanitization can be accomplished in only a few seconds with an intense UV light source, care must be taken to avoid both direct exposure to human eyes and prolonged exposure to skin. In the preferred embodiment, a less intense light intensity (such as 5 mW bulbs at a distance of 3 inches) is utilized which takes approximately 2 seconds to be effective. This lower intensity light source provides a safer design for the UV sanitizer station 106, which is suitable for public use.

Nonetheless, even with this lower intensity light source, repeated use of the UV sanitizer station 100 may be considered unsafe. In particular, such repeated use may cause skin damage. To prevent such consequences, in one embodiment, the exposure limiter 132, which is discussed below with reference to FIG. 4, enforces a safe use standard using facial recognition technology. In one embodiment, the exposure limiter 132 ensures that a user does not receive more exposure than a predefined defined exposure limit also referred to occasionally herein as a safe use standard.

Since light from the UV light source 222 is not always visible to the user during use, the blower 224 blows a stream of air onto the user's hand during this exposure. When the processor 230 turns off the light source 222 and the blower 224 at the end of the exposure time, the user will detect that the blowing has stopped and will know that the UV exposure is also completed.

In one embodiment, the UV sanitizer station 106 provides content 244 such as advertisements to the user during the UV exposure. This content may include typically A/V presentations that are stored in memory 240, and then presented by the processor 230 over the display 210 and speaker 212. In one embodiment, the content is an advertisement that runs for approximately the same duration as the UV germicidal exposure duration. In one embodiment, when the content 244 and the concurrent UV exposure are complete, the UV sanitizer station 106 preferably presents supplemental content to the user such as a promotion relating to the advertised product or service, such as a percentage off promotion, a buy-one-get-one-free promotion, or a cash discount promotion. In one embodiment, the content 244 includes the details for each promotion and is stored in the memory 240 and the promotions are associated with the various advertisements which are also stored as content 244 in the memory 240.

In one embodiment, the methods and system herein enable a user to select the content presented to the user for the duration of the UV exposure. In one embodiment, the content selector 134, which is described below with reference to FIG. 5, enables a user to perform a touch-less (e.g. without touching the display 210 or another input device) selection of the content, thereby beneficially reducing the user's exposure to bacteria, viruses, microorganisms and other contaminants that often reside on such surfaces.

In a preferred embodiment, the UV sanitizer station 106 includes a communications unit 250 that allows the UV sanitizer station 106 to communicate with a remote server 122 over a network 102. In one embodiment, the server 122 uses a database to track the locations and identities of the various stations 106*a-n*.

In a preferred embodiment, the server 122 is responsible for maintaining and updating the exposure limiter 132, the content selector and the content 244 found in the memory 240 of the UV sanitizer station 100. In one embodiment, the server 122 maintains available content 244 (e.g. ads and promotions) in a database and periodically makes this data available for download to the UV sanitizer station 106. In one embodiment, the UV sanitizer station 106 transmits information about ads displayed and promotions presented by the station 100 to the server 122 for storage in its database as elements.

In one embodiment, the UV sanitizer station 106 provides to the server 122 facial data and usage data that it collects. In a preferred embodiment, the server 122 collects this facial data and usage data (occasionally referred to as exposure data) from a plurality of UV sanitizer stations 106. This allows the server 122 or a database associated therewith to be the repository of all usage data for all of the UV sanitizer stations 106. In one embodiment, this centralized usage/exposure data is downloaded back to each UV sanitizer station 106 to supplement the local data 248. In this way, each UV sanitizer station 106 can use usage data from all of the UV sanitizer stations 106 when determining whether an additional use by the currently identified user will exceed its safe use standard.

In one embodiment, the server 122 assigns the facial data of each separately identifiable individual to a particular user identifier. This user ID can be used to link usage data with the facial data simply by assigning each usage event in the usage data to the appropriate user identifier. In some embodiments, a particular user ID may be associated with several facial data records in the facial data. This is because the facial recognition analysis of multiple images of the same individual will contain slightly different facial feature information, as each image will be scored slightly differently by the facial recognition algorithms used by the UV sanitizer station 106. Although the scores will be close enough for the UV sanitizer station 106 and the server 122 to identify the facial images as relating to the same person, it can be useful to save the characteristics of each image in the facial data in order to develop a more complete profile of that user's face.

Figure 3:
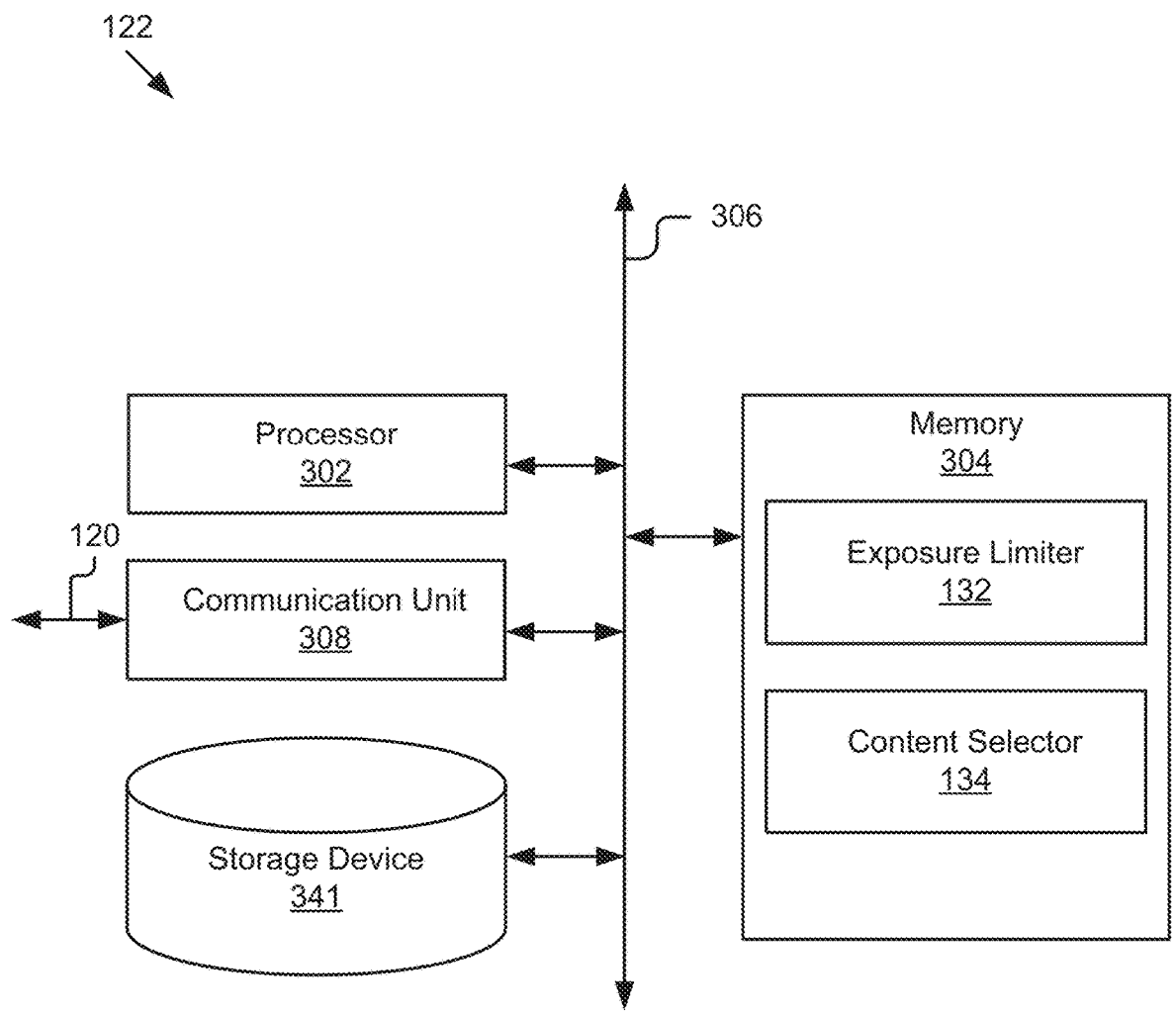
FIG. 3 is a block diagram of an example server according to one embodiment.

FIG. 3 is a block diagram of server 122 according to one embodiment. The server 122, as illustrated, may include a processor 302, a memory 304, a communication unit 308, and a storage device 341, which may be communicatively coupled by a communications bus 306. The server 122 depicted in FIG. 3 is provided by way of example and it should be understood that it may take other forms and include additional or fewer components without departing from the scope of the present disclosure. For example, while not shown, the server 122 may include input and output devices (e.g., a display, a keyboard, a mouse, touch screen, speakers, etc.), various operating systems, sensors, additional processors, and other physical configurations.

The processor 302, memory 304 and bus 306 may be similar to the processor 230, memory 240 and bus 232 of the hand sanitizer station 106 described above. Depending on the embodiment, the exposure limiter 132 may be included in the server 122 (e.g. as illustrated in FIGS. 1 and 3), included in the hand sanitizer station 106 (e.g. as illustrated in FIG. 2B) or included in both the hand sanitizer station 106 and the server 122. Similarly, depending on the embodiment, the content selector may be included in the server 122 (e.g. as illustrated in FIGS. 1 and 3), included in the hand sanitizer station 106 (e.g. as illustrated in FIG. 2B) or included in both the hand sanitizer station 106 and the server 122.

The communication unit 308 is similar to communications unit 250 of the hand sanitizer station 106 and may include one or more interface devices (I/F) for wired and/or wireless connectivity with the network 102. For instance, the communication unit 208 may include, but is not limited to, CAT-type interfaces; wireless transceivers for sending and receiving signals using radio transceivers (4G, 3G, 2G, etc.) for communication with the mobile network 103, and radio transceivers for Wi-Fi™ and close-proximity (e.g., Bluetooth®, NFC, etc.) connectivity, etc.; USB interfaces; various combinations thereof; etc. In some implementations, the communication unit 308 can link the processor 302 to the network 102, which may in turn be coupled to other processing systems. The communication unit 308 can provide other connections to the network 102 and to other entities of the system 100 using various standard network communication protocols.

The storage device 341 is an information source for storing and providing access to data. In some implementations, the storage device 341 may be coupled to the components 302, 304, and 308 of the computing device via the bus 306 to receive and provide access to data. In some implementations, the storage device 341 may store various data in one or more databases. For example, in one embodiment, the storage device 341 includes one or more databases (not shown) storing UV sanitizer 106 locations, available content (e.g. ads and promotions), presented content (e.g.

ads and promotions), redeemed content (e.g. redeemed promotions), facial data, usage/exposure data, etc.

The storage device 341 may be included in the server 122 and/or a storage system distinct from but coupled to or accessible by the server 122. The storage device 341 can include one or more non-transitory computer-readable mediums for storing the data. In some implementations, the storage device 341 may be incorporated with the memory 304 or may be distinct therefrom. In some implementations, the storage device 341 may include a database management system (DBMS) operable on the server 122. For example, the DBMS could include a structured query language (SQL) DBMS, a NoSQL DMBS, various combinations thereof, etc. In some instances, the DBMS may store data in multi-dimensional tables comprised of rows and columns, and manipulate, i.e., insert, query, update and/or delete, rows of data using programmatic operations.

As mentioned above, the server 122 may include other and/or fewer components. Examples of other components may include a display, an input device, a sensor, etc. (not shown). In one embodiment, the server 122 includes a display. The display may display electronic images and data output by the client device 106 for presentation to a user 112. The display may include any conventional display device, monitor or screen, including, for example, an organic light-emitting diode (OLED) display, a liquid crystal display (LCD), etc. In some implementations, the display may be a touch-screen display capable of receiving input from a stylus, one or more fingers of a user 112, etc. For example, the display may be a capacitive touch-screen display capable of detecting and interpreting multiple points of contact with the display surface.

The input device (not shown) may include any device for inputting information into the server 122. In some implementations, the input device may include one or more peripheral devices. For example, the input device may include a keyboard (e.g., a QWERTY keyboard or keyboard in any other language), a pointing device (e.g., a mouse or touchpad), microphone, an image/video capture device (e.g., camera), etc. In some implementations, the input device may include a touch-screen display capable of receiving input from the one or more fingers of the user 112.

Example Exposure Limiter 132

Figure 4:
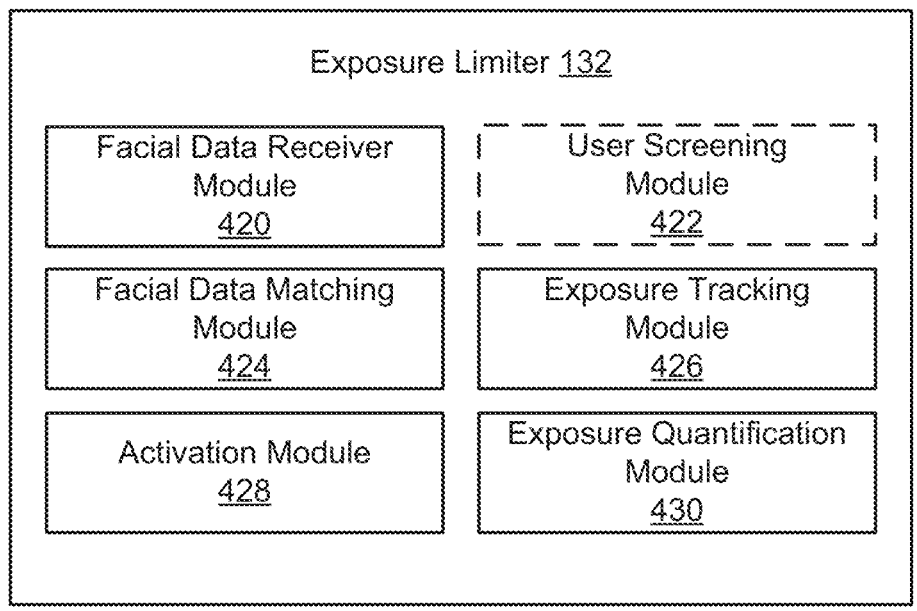
FIG. 4 is a block diagram of an example exposure limiter according to one embodiment.

Referring now to FIG. 4, the exposure limiter 132 is shown in more detail according to one embodiment. FIG. 4 is a block diagram of the exposure limiter 132 included in a computing device (e.g., a server 122 and/or hand sanitizing station 106) according to one embodiment.

In one embodiment, the exposure limiter 132 comprises a facial data receiver module 420, an optional user screening module 422, a facial data matching module 424, an exposure tracking module 426, an activation module 428 and an exposure quantification module 430.

In some embodiments, a module as used herein includes code and routines for performing the features and functionalities described with reference to that module. In one embodiment, the module is a set of instructions executable by the processor 230/302. In another embodiment, the module is stored in the memory 240/304 and is accessible and executable by the processor 230/302. In either embodiment, the module is adapted for cooperation and communication with the processor 230/302, other components of the hand sanitizer station 106/server 122 and other components of the exposure limiter 132.

It will be recognized that the modules 420, 422 (optional), 424, 426, 428, 430 comprised in the exposure limiter 132 are not necessarily all on the same computing device. In one embodiment, the modules 420, 422 (optional), 424, 426, 428, 430 and/or their functionality are distributed across multiple computing devices. For example, in one embodiment, the facial data receiver module 420, user screening module 422, activation module 428 and exposure quantification module 430 are included in a hand sanitizer station 106 and the other modules 424 and 426 are included in a server 122. Such embodiments may allow for increased speed/performance, reduced network load, comparisons of facial data centrally stored and maintained and received from multiple hand sanitizing stations, or other benefits. It will be recognized that the preceding is just an example of distributing modules across multiple computing devices (e.g. 106a and 122) and that other examples exist. It will be further recognized that the functionality of any particular module may be distributed across multiple computing devices (e.g. multiple servers 122).

The facial data receiver module 420 receives facial data based on an image captured at the hand sanitizer station. In one embodiment, the camera of a hand sanitizer station automatically captures an image upon detecting an initiation event. An initiation event may vary based on the embodiment. Examples of an initiation event include, but are not limited to, detecting a user (or other object) positioned in front of the hand sanitizer station, detecting that the user has positioned the user's hands (or other object) for sanitation, etc. It should be recognized that the preceding are just examples of initiation events and other exist and are within the scope of disclosure. It should also be recognized that the initiation events may be detected based on sensor inputs from one or more sensors e.g., weight sensors on a pad placed in front of the hand sanitizer station to detect when a user is in front of the hand sanitizer, acoustic sensors (e.g. ultrasound, sonar, microphone, etc.) to detect the presence of a user and/or the user's hands, thermal sensors (e g infrared) to detect the presence of a user and/or the user's hands, optical sensors (e.g. laser or laser range finder) to detect the presence of a user and/or the user's hands, image sensors (e.g. a camera and image processor to determine when a user is present and facing the sensor), etc.

The facial data receiver module 420 receives facial data based on an image captured at the hand sanitizer station. In one embodiment, the facial data receiver module 420 receives an image of a face captured by a camera 214 of the hand sanitizer 106 as facial data. In another embodiment, the facial data receiver module 420 receives a representation of a face generated from an image of a face captured by the hand sanitizer station 106. For example, in one embodiment, the facial data receiver module 420 receives data based on landmarks of a face including, for example, the corners of a user's mouth, the user's nose, the corners of the user's eyes, etc. as facial data. It should be recognized that the preceding are just examples of facial data and examples of facial data and that others exist and their use is contemplated and within the scope of the disclosure herein. It should be recognized that the description herein refers to facial data throughout the description of the exposure limiter 132. However, it should be noted that, in some embodiments, the form of the facial data may vary from module to module and/or at different stages of the facial recognition process. For example, in one embodiment, the facial data receiver module 420 may receive the raw image that includes a user's face captured by the camera 214 of the hand sanitizing station 106 (i.e. a first type of facial data) and identify landmarks of facial features (i.e. a second type of facial data) and the user screening module 422 or another module of the exposure limiter 132 utilizes those landmarks (i.e. the second type of facial data) as the facial data for performing the functionality associated with that module.

In one embodiment, the facial data receiver module 420 passes the facial data to one or more of the user screening module 422 and the facial data matching module 424. For example, the facial data receiver module 420 is communicatively coupled to one or more of the user screening module 422 and the facial data matching module 424 to send the facial data to one or more of the user screening module 422 and the facial data matching module 424. In another embodiment, the facial data receiver module 420 stores the facial data in the storage device 341 (or any other non-transitory storage medium communicatively accessible). The other modules of the facial data receiver module 420 including, e.g., the user screening module 422 and the facial data matching module 424, can retrieve the facial data by accessing the storage device 341 (or other non-transitory storage medium).

The optional user screening module 422 screens users based on the facial data itself. For example, the user screening module 422 screens users using one or more of approximate height, age, developmental stage (e.g. adult adolescent, child), etc. based on the facial data itself. In one embodiment, the user screening module 422 analyzes the facial data to determine an approximate height of the user. For example, the user screening module 422 uses a known height and angle at which the camera is mounted on the hand sanitizing station to calculate an approximate height of the user from the facial data (e.g. if the user's face appeared lower X portion of the frame, the user is likely short and between X and Y inches tall). In one embodiment, the user screening module 422 analyzes the facial data to determine an approximate age of the user. For example, the user screening module 422 uses one or more ratios and/or proportions associated with facial features to approximate the age of the user. Therefore, the user screening module 422 beneficially provides a mechanism for identifying users having certain physical characteristics such as children who are typically short with faces that have ratios and proportions associated with youth and prohibiting them from exposure to the UV light.

In one embodiment, when the user screening module 422 screens a user (e.g. determines the user is likely a child based on the facial data), the user screening module 422 passes a "Deny" message to the activation module 428 and the activation module 428 does not activate the UV source 222. For example, the user screening module 422 is communicatively coupled to the activation module 428 to send the "Deny" message to the activation module 428. In another embodiment, the user screening module 422 stores the "Deny" message in the storage device 341 (or any other non-transitory storage medium communicatively accessible). The other modules of the exposure limiter including, e.g., the activation module 428, can retrieve the "Deny" message by accessing the storage device 341 (or other non-transitory storage medium).

In an embodiment, that omits the user screening module 422 or in another embodiment that includes the user screening module 422 and in which the user is not screened by the user screening module 422, the facial data matching module 424 identifies whether the facial data matches facial data associated with a previous use of a hand sanitizer station.

The facial data matching module 424 determines whether the facial data received by the facial data receiver module 420 matches facial data of a previous use of a hand sanitizer station. For example, in one embodiment, the facial data matching module 424 accesses a database of stored facial data each associated with one or more previous uses of a hand sanitizer station and determines whether the facial data received by the facial data receiver module 420 matches facial data from the database.

In one embodiment, when the facial data matching module 424 determines that there is a match between the facial data received by the facial data receiver module 420 for a current/immediate user and facial data associated with a previous use of a hand sanitizer station, the facial data matching module 424 identifies the match to the exposure tracking module 426 and the exposure tracking module 426 obtains the exposure data associated with that facial data. To summarize and simplify, the facial data matching module 424 determines if the current user of the hand sanitizer station has previously used a hand sanitizer station based on whether there is a match and the exposure tracking module 426 will obtain the data associated with that user or, according to one embodiment, that user's facial data.

In one embodiment, the facial data matching module 424 passes the identification of the match to the exposure tracking module 426. For example, the facial data matching module 424 is communicatively coupled to the exposure tracking module 426 to send the identification of the match to the exposure tracking module 426. In another embodiment, the facial data matching module 424 stores the identification of the match in the storage device 341 (or any other non-transitory storage medium communicatively accessible). The other modules of the exposure limiter 132 including, e.g., the exposure tracking module 426, can retrieve the identification of the match by accessing the storage device 341 (or other non-transitory storage medium).

In one embodiment, when the facial data matching module 424 determines that there is no match between the facial data received by the facial data receiver module 420 and facial data associated with a previous use of a hand sanitizer station 106, the facial data matching module 424 identifies the absence of a match to the exposure tracking module 426 and the exposure tracking module 426 creates a new user to track and stores the facial data associated with that new user.

Depending on the embodiment, the facial data associated with a previous uses of a hand sanitizer station may be stored locally at the hand sanitizing station 106, remotely at the server 122 or both. In one embodiment, the facial data associated with a previous uses of a hand sanitizer station used by the facial data matching module 424 is not limited to facial data associated with a previous uses of a hand sanitizer station for previous uses of that single machine. For example, in some embodiments, the facial data associated with a previous uses of a hand sanitizer station is a comprehensive collection of facial data associated with a previous uses of a hand sanitizer station across multiple hand sanitizer stations 106. Such embodiments may beneficially allow enforcement of a safe use limit regardless of whether the user repeatedly uses the same hand sanitizer station 106 or uses different hand sanitizer stations 106 in series.

In one embodiment, the comprehensive facial data associated with previous uses of a hand sanitizer station is stored in a central database (e.g. on storage device 341 of the server 122). In one embodiment, a copy of the comprehensive facial data associated with previous uses of a hand sanitizer station is copied to the hand sanitizer station 106 from the central database maintained by the server 122. In another embodiment, the comprehensive facial data associated with a previous uses of a hand sanitizer station is stored in a locally (e.g. in the memory 240 of each hand sanitizer station 106 and synchronization messages are exchanged between the hand sanitizer stations 106 to maintain the comprehensiveness and accuracy of the facial data associated with a previous uses of a hand sanitizer station at each of the hand sanitizer stations 106 in the system).

In one embodiment, the facial data matching module 424 passes the absence of the match to the exposure tracking module 426. For example, the facial data matching module 424 is communicatively coupled to the location determination module 328 to send the absence of the match to the exposure tracking module 426. In another embodiment, the facial data matching module 424 stores the absence of the match in the storage device 341 (or any other non-transitory storage medium communicatively accessible). The other modules of the exposure limiter 132 including, e.g., the exposure tracking module 426, can retrieve the absence of a match by accessing the storage device 341 (or other non-transitory storage medium).

The exposure tracking module 426 tracks user UV exposure. In one embodiment, the exposure tracking module 426 tracks user UV exposure by recording one or more metrics associated with UV exposure in association with a user or a user's facial data. The one or more metrics tracked and recorded by the exposure tracking module 426 may vary depending on the embodiment. Examples of metrics associated with UV exposure include, but are not limited to, number of exposures (e.g. how many time the user has sanitized his/her hands), duration of exposure (e.g. seconds or milliseconds), intensity/brightness of exposure (e.g. microwatts per square centimeter or using a proxy such as the wattage of the UV bulb used in the hand sanitizing station 106), frequency of exposure (e.g. number of exposures per hour/day/week/etc.), a function of the previously mentioned metrics (e.g. a sum of the product of the duration of exposure the radiation intensity measured in microwatts per square centimeter for each exposure for the last X hours), etc.

In one embodiment, the exposure tracking module 426 uses a table or other data structure to organize exposure data on a per user basis. For example, in one embodiment, each set of facial data which is uniquely associated with a user's face is associated with a row in a table and the row stores the exposure data such as one or more of the metrics above. In one embodiment, when the facial data matching module 424 identifies a match, the exposure tracking module 426 obtains the exposure data associated with the identified matching facial data. In one embodiment, when the facial data matching module 424 identifies an absence of a match, the exposure tracking module 426 creates a new user and tracks the exposure of that new user. For example, the exposure tracking module 426 adds a row to the table and associates the facial data with that row.

Depending on the embodiment, the exposure data may be stored locally at the hand sanitizing station 106, remotely at the server 122 or both. In one embodiment, the exposure data obtained by the exposure tracking module 426 is not limited to exposure data for users of a single machine. For example, in some embodiments, the exposure data is a comprehensive collection of exposure data across multiple hand sanitizer stations 106. Such embodiments may beneficially allow enforcement of a safe use limit regardless of whether the user repeatedly uses the same hand sanitizer station 106 or uses different hand sanitizer stations 106 in series.

In one embodiment, the exposure data (occasionally referred to herein as usage data is shared with a server computer system 122. The server 122, in turn, shares this data with multiple UV sanitizer stations 106 to prevent excessive use by a single user across multiple stations. In one embodiment, the comprehensive exposure data including the one or more metrics and associated with facial recognition data is stored in a central database (e.g. on storage device 341 of the server 122). In one embodiment, a copy of the comprehensive exposure data including the one or more metrics and associated with facial recognition data is copied to the hand sanitizer station 106 from the central database maintained by the server 122. In another embodiment, the comprehensive exposure data including the one or more metrics and associated with facial recognition data is stored in a locally (e.g. in the memory 240 of each hand sanitizer station 106 and synchronization messages are exchanged between the hand sanitizer stations 106 to maintain the comprehensiveness and accuracy of the exposure data at each of the hand sanitizer stations 106 in the system).

In one embodiment, exposure tracking module 426 updates the exposure data based on information received from the exposure quantification module 430, which is discussed below.

Depending on the embodiment, the facial data associated with the exposure data may vary. In some embodiments, only the most recent facial data is stored in association with the one or more metrics. For example, when the facial data matching module 424 identifies a match between the facial data of the user present at the hand sanitizer station and received by the facial data receiver module 420 with facial data associated with a previous use (or attempted use), the exposure tracking module 426 over-writes the facial data associated with a previous use facial data associated with a previous use with the facial data of the user present at the hand sanitizer station 106 and received by the facial data receiver module 420. In some embodiments as mentioned above, multiple sets of facial data are associated with exposure data for a single user in order to have a more complete representation of the user's face and feature set. In some embodiments, the facial data stored is merely a mathematical representation of facial features and characteristics and cannot be used to reverse engineer a user's facial features or an image thereof.

In some embodiments, user identification information other than facial data is not stored. For example, there is no name or other personal identification associated the facial data and metrics data. Such an embodiment, may increase privacy and anonymity for the user which may be desirable. However, in some embodiments, a user can register and provide user identification information in addition to facial data for storage and association. For example, assume an employee of a food chain registers with the system 100 and provides one or more of an employee number, name, phone number, e-mail address, or some other personal information. In one embodiment, the personal information may be stored with the facial data of that user and the exposure data metrics. Such an embodiment particularly if coupled with RFID, Beacon, or other physical tracking technology may beneficially allow an employer to track whether an employee is complying with company policy or a government regulations (e.g. sanitizing their hands regularly and/or after visiting the restroom, etc.).

In some embodiments, exposure data and facial data may time-out and be expunged from the system 100. For example, assume that the safe use/exposure limitation is based on a 24 hour period. In one embodiment, the exposure tracking module 426 may expunge all facial data and associated usage metrics more than 24 hours old. In one embodiment, as metrics associated with usage outside that 24 hour period time-out totals (e.g. cumulative usage over the past 24 hours) may be recalculated.

In one embodiment, the exposure tracking module 426 passes the exposure data to the activation module 428. For example, the exposure tracking module 426 is communicatively coupled to the activation module 428 to send the exposure data to the activation module 428. In another embodiment, the exposure tracking module 426 stores the exposure data in the storage device 341 (or any other non-transitory storage medium communicatively accessible). The other modules of the exposure limiter 132 including, e.g., the activation module 428, can retrieve the exposure data by accessing the storage device 341 (or other non-transitory storage medium).

The activation module 428 determines whether the UV lamp of the hand sanitizer station 106 is activated to sanitize the user's hands based on the exposure data and a safe use standard (occasionally referred to herein as an exposure limit). In one embodiment, the activation module 428 determines not to activate the UV source 222 of the hand sanitizer station 106 to sanitize the user's hands when the exposure data indicates that the user has already met or exceed the safe use/exposure limitation or, in some embodiment, when an activation would cause the user to meet or exceed the safe use/exposure limitation. The safe use/exposure limitation may vary depending on the embodiment. In one embodiment, the safe use/exposure limit may be based on one or more of the metrics discussed above with reference to exposure data.

The exposure quantification module 430 quantifies the user's UV exposure from the hand sanitation process. The quantification performed by the exposure quantification module 430 varies depending on the embodiment and typically coincides with the metrics maintained by the exposure tracking module 426. For example, assume the safe use/exposure limit is based solely on a number of uses; in one embodiment, the exposure tracking module 426 may only track a number of uses and the exposure quantification module 430 may only determine whether an activation occurred and the number of uses should be incremented in the exposure data.

In one embodiment, the exposure quantification module 430 quantifies the user's UV exposure from the hand sanitation process explicitly based on measurements. For example, in one embodiment, the one or more sensors 126 of the hand sanitizer station 106 include a photo sensor and the exposure quantification module 430 receives data from the photo sensor (e.g. a radiation intensity and duration) of the user's exposure during the hand sanitation process and uses those measurements to quantify the user's exposure.

In one embodiment, the exposure quantification module 430 quantifies the user's UV exposure from the hand sanitation process implicitly. For example, in one embodiment, the exposure quantification module 430 may track the number of activations of the UV light source (which in some embodiments may be of a fixed duration) since the light source (e.g. bulb) was last replaced and use an experimentally derived curve that represents the decay of the UV light source's performance as the bulb is used to determine how much exposure the user received during the hand sanitation process.

In one embodiment, the exposure quantification module 430 quantifies the user's UV exposure from the hand sanitation process both implicitly and explicitly. For example, in one embodiment, the exposure quantification module 430 may use sensors to track durations (which are varied in one embodiment to maintain a level of exposure sufficient for sanitization as the bulb progressively dims through its life-cycle) of activations of the UV light source since the light source (e.g. bulb) was last replaced and uses an experimentally derived curve that represents the decay of the UV light source's performance as the bulb is used to determine how much exposure the user received during a particular hand sanitation process.

In one embodiment, the exposure quantification module 430 provides the quantified UV exposure to the exposure tracking module 426 to update the exposure data. In one embodiment, the exposure quantification module 430 provides the quantified UV exposure to the activation module 428 for the activation module 428 to adjust the duration of the activation of the UV light source (e.g. to increase the duration as the UV light source 222 ages and loses intensity/effectiveness).

In one embodiment, the exposure quantification module 430 passes the quantified UV exposure to one or more of the exposure tracking module 426 and the activation module 428. For example, the exposure quantification module 430 is communicatively coupled to one or more of the exposure tracking module 426 and the activation module 428 to send the quantified UV exposure to one or more of the exposure tracking module 426 and the activation module 428. In another embodiment, the exposure quantification module 430 stores the quantified UV exposure in the storage device 341 (or any other non-transitory storage medium communicatively accessible). The other modules of the exposure limiter 132 including, e.g., one or more of the exposure tracking module 426 and the activation module 428, can retrieve the quantified UV exposure by accessing the storage device 341 (or other non-transitory storage medium).

Example Content Selector 134

Figure 5:
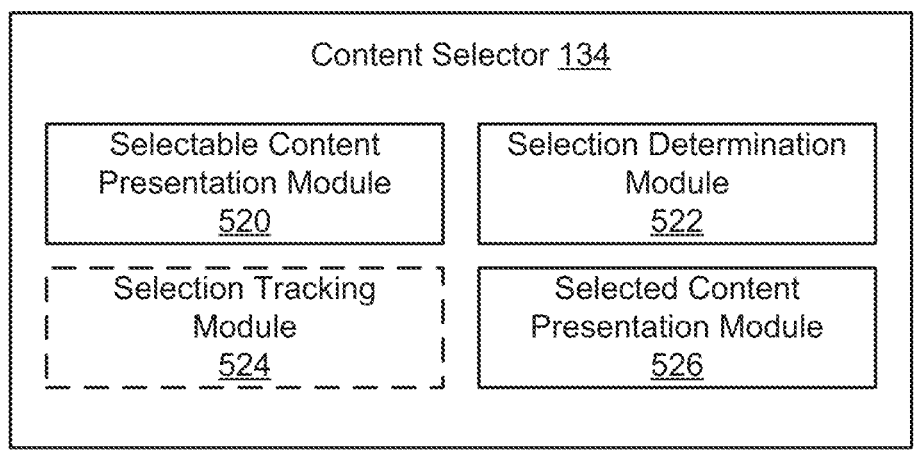
FIG. 5 is a block diagram of an example content selector according to one embodiment.

Referring now to FIG. 5, the content selector 134 is shown in more detail according to one embodiment. FIG. 5 is a block diagram of the content selector 134 according to one embodiment. The content selector 134 enables a touchless user selection of content to be presented to the user during the UV hand sanitation process.

In one embodiment, the content selector 134 comprises a selectable content presentation module 520, a selection determination module 522, an optional selection tracking module 524 and a selected content presentation module 526.

In some embodiments, a module as used herein includes code and routines for performing the features and functionalities described with reference to that module. In one embodiment, the module is a set of instructions executable by the processor 230/302. In another embodiment, the module is stored in the memory 240/304 and is accessible and executable by the processor 230/302. In either embodiment, the module is adapted for cooperation and communication with the processor 230/302, other components of the hand sanitizer station 106/server 122 and other components of the content selector 134.

It will be recognized that the modules 520, 522, 524, 526 comprised in the content selector 134 are not necessarily all on the same computing device. In one embodiment, the modules 520, 522, 524, 526 and/or their functionality are distributed across multiple computing devices. For example, in one embodiment, the selection tracking module 524 is included in a server 122 and the other modules are included in a hand sanitizer station 106. It will be recognized that the preceding is just an example of distributing modules across multiple computing devices (e.g. 106a and 122) and that other examples exist.

The selectable content presentation module 520 presents graphic elements associated with content eligible for selection by the user. Examples of such graphic elements include, but are not limited to icons, animations, video clips, thumbnails, etc. In some embodiments, the content includes one or more advertisements. For example, in one embodiment, the content eligible for display includes advertisements associated with the location in which the hand sanitizing station is located. For example, in a preferred embodiment, the hand sanitizer station would be located in a public area of Retailer A and present graphic elements associated with advertisements for products sold by Retailer A.

Figure 9:
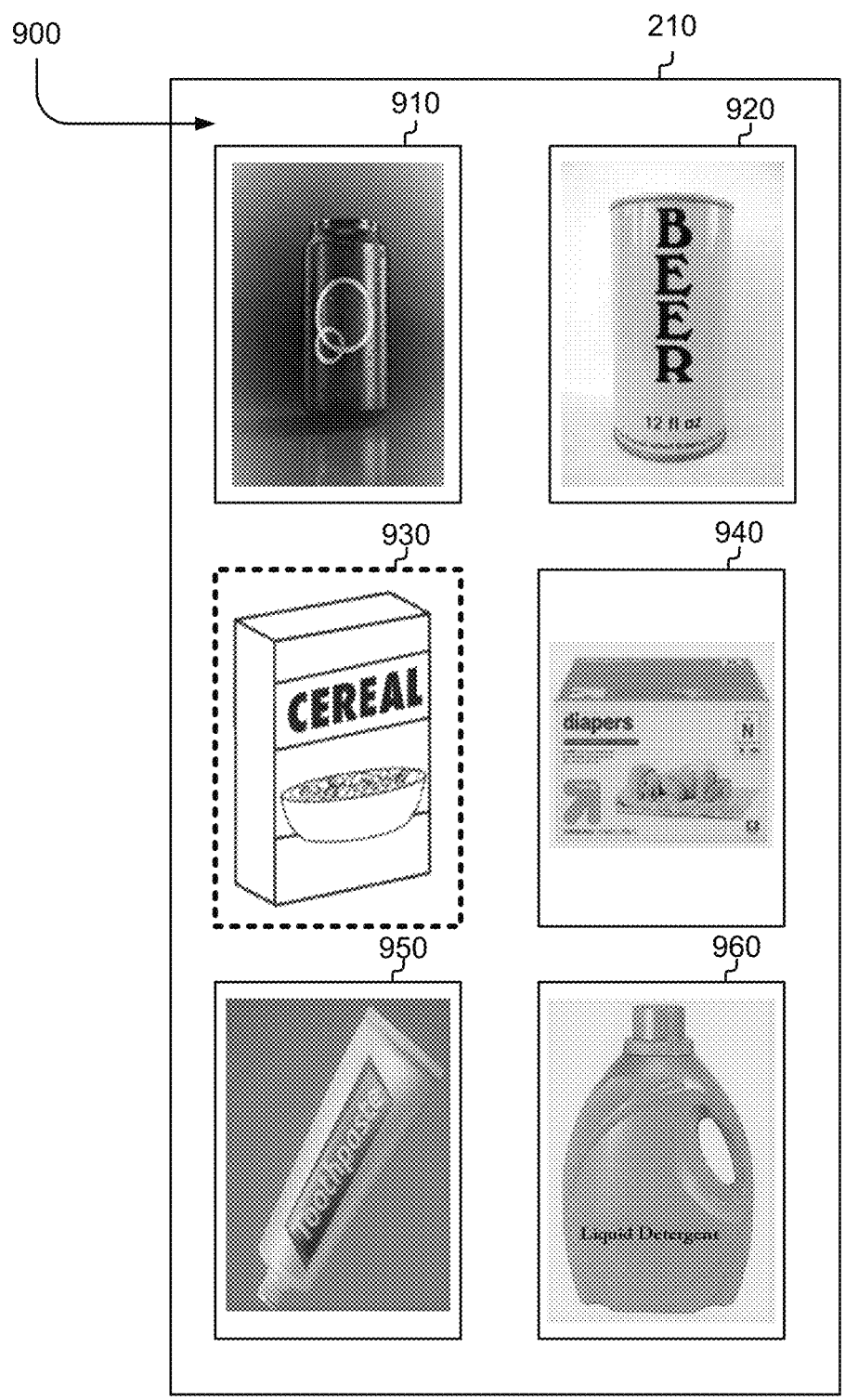
FIG. 9 is block diagram of an example user interface for touch-less user content selection at a UV hand sanitizer station according to one embodiment.

In preferred embodiments, the content selector 134 enables the user to select content such as an advertisement without touching the hand sanitizer station 106 and risking further contamination through touch. Depending on the embodiment, the touchless selection of content may use different sensors and mechanisms and the selectable content presentation module 520 presents the content eligible for selection by the user based on the sensors and touch-less mechanism used. For example, referring to FIG. 9, in some embodiments, the sanitizer station's display 210 is divided up into various sections each presenting a graphic element 910, 920, 930, 940, 950, 960 associated with an advertisement. While FIG. 9 illustrates six graphic elements 910, 920, 930, 940, 950, 960 arranged in a grid two graphic elements wide and three tall, it should be recognized that FIG. 9 is merely an example according to one embodiment, and any number of graphic elements may be presented in any format.

In one such embodiment, the selectable content presentation module 520 presents these graphic elements and then cycles through the presented graphical items highlighting (or otherwise visually distinguishing) one at a time. For example, in the illustrated embodiment of FIG. 9, the dashed line indicates that graphic element 930 is presently highlighted. After a period of time (e.g. 1-3 seconds), graphic element 930 would no longer be highlighted and graphic element 940 would be highlighted absent a selection by the user. In another such embodiment, one or more micro-sonar sensors are located behind the display and the user may use his fingers and gesture close to, but without touching, the display 210 and the selectable content presentation module 520 presents these graphic elements and highlights (or otherwise visually distinguishes) the graphic element 930 based on the gestures. In still other such embodiment, a user's eyes' pupils may be tracked to determine which graphic element associated with content to highlight. In yet another embodiment, the user may make gestures that are picked up by one or more cameras 214 of the sanitizer station 106 and highlights a graphic element based on those gestures.

In one embodiment, the selectable content presentation module 520 receives updated content (e.g. new ads and promotions) for potential presentation to users from the server 122. For example, the selectable content presentation module 520 may receive updated content (e.g. new ads and promotions) for potential presentation to users from the server 122 on a weekly basis when a retailer changes its ads and promotions weekly.

The selection determination module 522 determines which content eligible for selection is selected for presentation to the user. In a preferred embodiment, the content selected for presentation is the content associated with the highlighted graphic element when the hand sanitizer station 106 sensor 126 detects that the user has place his/her hands or another object into the compartment. For example, referring again to FIG. 9, graphic element 930 is presently highlighted, so, in one embodiment, if a user was to place his/her hands in the compartment 220 of the station 106, the advertisement for cereal associated with graphic element 930 is presented to the user during the UV sanitation cycle.

The selection tracking module 524 is optional and may be omitted in some embodiments. In one embodiment, the selection tracking module 524 tracks and provides data and analytics regarding the content presented to users. Examples may include, but are not limited to, one or more of views, unique views, demographics of viewers, identifiers for viewers, etc. In one embodiment, the selection tracking module 524 tracks and provides data and analytics regarding the supplemental content including, e.g. the number of redemptions of promotions and coupons, redemption rates, characteristics of redeemers, etc. The data tracked by the selection tracking module may be stored by one or more of the server 122 and the hand sanitizer station 106.

The selected content presentation module 526 presents content which may include one or more of advertisements and promotions. In one embodiment, the selected content presentation module 526 presents content concurrently with hand sanitation process (e.g. while the UV light source and blower are on). In one embodiment, the selected content presentation module 526 presents content having a run-time/duration approximately the same as the duration of the UV exposure for the hand sanitation process.

In one embodiment, the selected content presentation module 526 may present supplemental content to the user after the hand sanitation and concurrent content (e.g. an advertisement) presentation have finished. For example, in one embodiment, the selected content presentation module 526 presents the user with a promotion or a coupon for the same product or a product related to the product that was the subject of the advertisement.

In one embodiment, the supplemental content is presented to the user by the selected content presentation module 526 using the display 210 of the sanitizer station 106. For example, in one embodiment, the selected content presentation module 526 presents a 1D barcode or a 2D barcode (e.g. a QR Code) to the user after the advertisement is played and the user may scan or take a picture to capture an image of that barcode and receive an electronic coupon/promotion associated with the barcode.

In one embodiment, the supplemental content is presented to the user by the selected content presentation module 526 using another channel. For example, in one embodiment, the selected content presentation module 526 prints a coupon/promotion associated with the product featured in the presented advertisement. In another example, in one embodiment, the selected content presentation module 526 pushes a coupon/promotion associated with the product featured in the presented advertisement to the user's mobile device (e.g. via a retailer specific app running on the user's mobile device, via an SMS text to which they may respond to receive a coupon, by identifying the user's mobile device through facial recognition, RFID of the mobile device, etc.).

In one embodiment, facial recognition such as that performed by the exposure limiter 132 may influence the content that is selected and presented to the user. For example, in one embodiment, the content selector 134 or one or more of its modules 520, 522, 524, 526 is communicatively coupled to access and/or receive information regarding the facial recognition performed and tracking data maintained by the exposure limiter 132. In one embodiment, when the content selector 134 determines (or is informed by the exposure limiter 132) that the user is a first time user or new user (e.g. those that have used a hand sanitizing station 106 less than X times or have not used the a hand sanitizing station 106 in the last Y months) based on facial data, the content selector 134 selects and presents educational content to educate that first-time/new user regarding one or more of how to operate the hand sanitizing station 106, the functions and services provided by the a hand sanitizing station 106, the benefits of hand sanitation, etc. In one such embodiment, when the content selector 134 determines (or is informed by the exposure limiter 132) determines that the user is not a first time user or new user based on facial data, the content selector 134 and its modules 520, 522, 524, 526 operate as described in the paragraphs above (e.g. allow a user to touch-lessly select an advertisement or other content for presentation rather than being presented the educational content).

Example Methods

Figure 6:
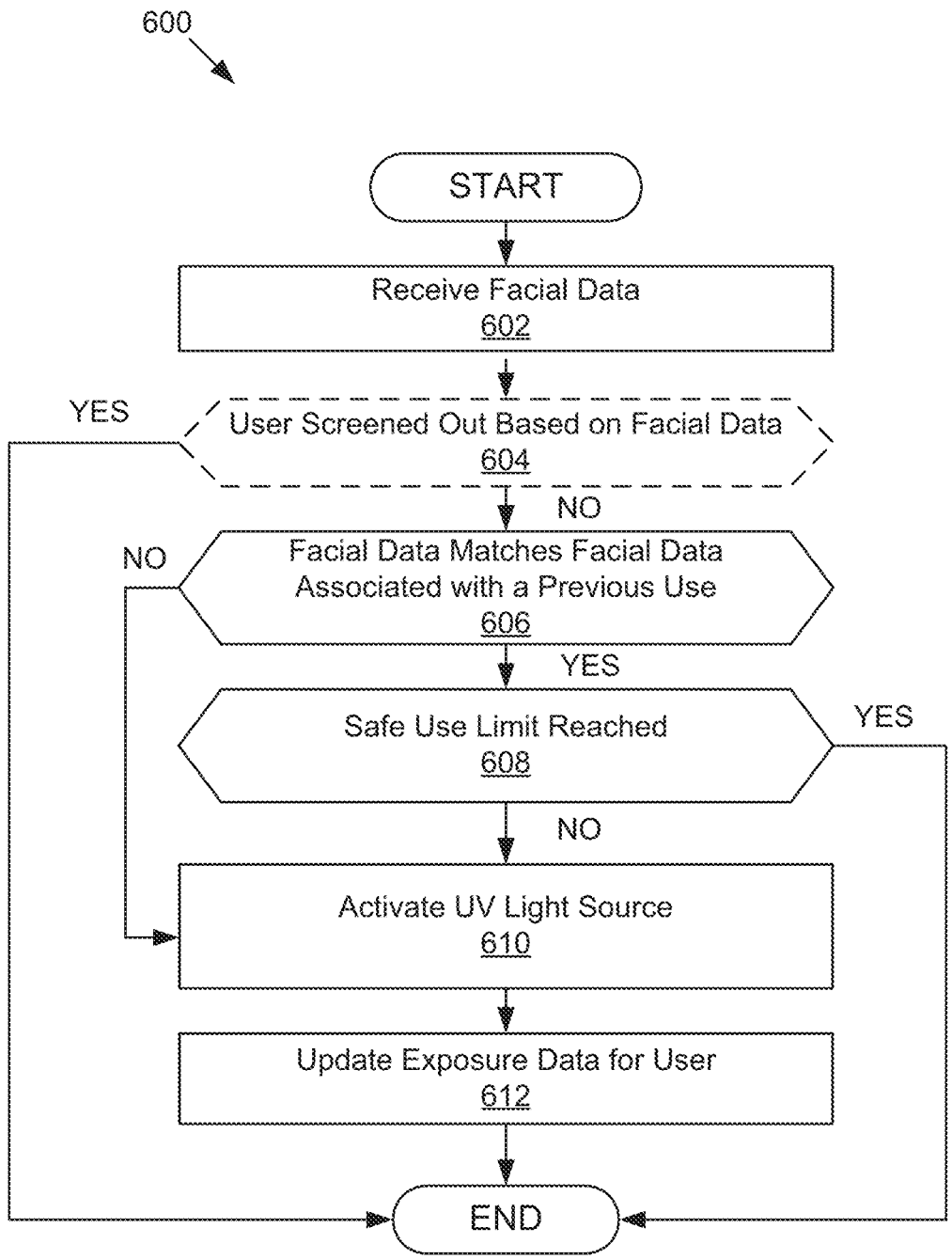
FIG. 6 is a flowchart of an example method for enforcing a safe use standard/exposure limit for a UV hand sanitizer based on facial recognition according to one embodiment.
Figure 7:
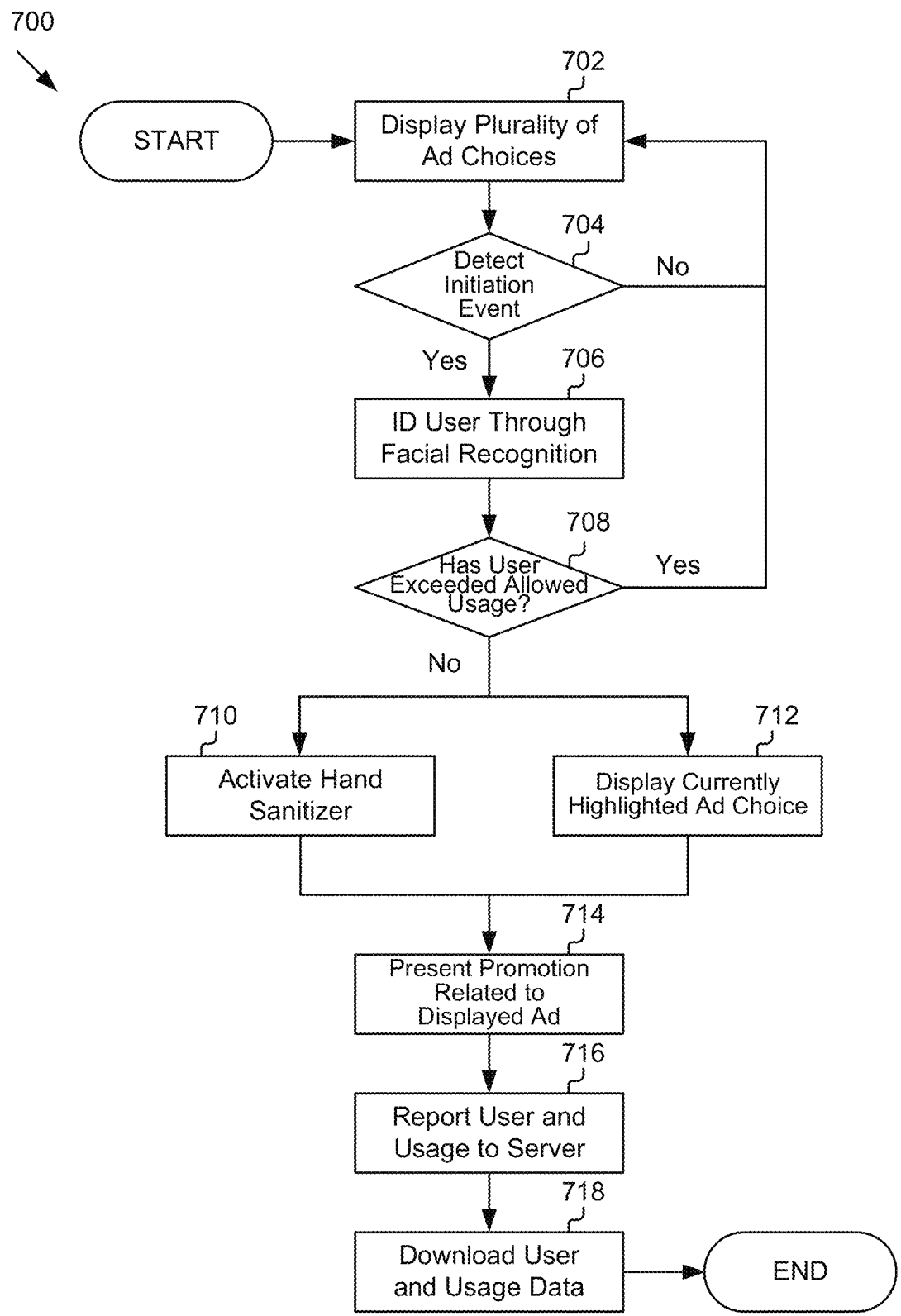
FIG. 7 is a flowchart of another example method for enforcing a safe use standard/exposure limit for a UV hand sanitizer based on facial recognition according to another embodiment.
Figure 8:
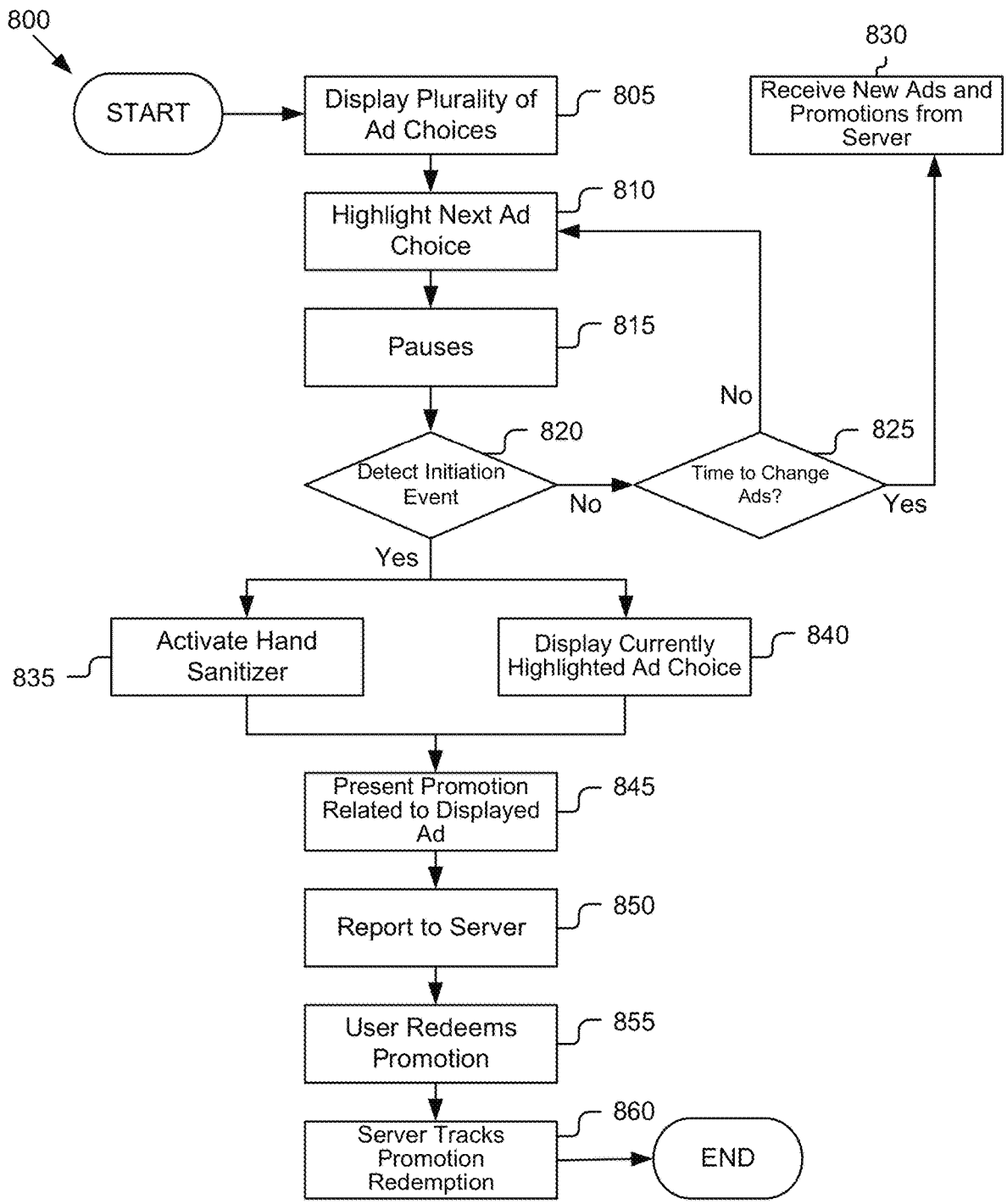
FIG. 8 is a flowchart of an example method for touch-less user content selection at a UV hand sanitizer station according to one embodiment.

FIGS. 6-8 depict various methods 600, 700, 800 performed by the system described above in reference to FIGS. 1-5. Steps that are optional or performed by optional modules are occasionally depicted in dashed boxes.

The process 600 for enforcing a safe use standard/exposure limit for a UV hand sanitizer station 106 based on facial recognition is shown in FIG. 6 according to one embodiment. This process 600 begins at step 602, with the facial data receiver module 420 receiving facial data. At step 604, when the optional user screening module 422 is included in the embodiment, the user screening module 422 determines whether the user should be screened out based on the facial data (e.g. height and age inferred based on characteristics of facial features). If the user screening module 422 determines that the user is to be screened out (604—yes), the method 600 ends and the UV light source is not activated. If the user screening module 422 determines that the user is not to be screened out (604—no), the method 600 continues at block 606.

At block 606, the facial data matching module 424 determines whether the facial data received at block 602 matches facial data associated with a previous hand sanitizer station use. If the facial data matching module 424 determines that the facial data received at block 602 does not match facial data associated with a previous hand sanitizer station use (606—no), the method 600 continues at block 610 and the activation module 428 activates the UV light source. If the facial data matching module 424 determines that the facial data received at block 602 matches facial data associated with a previous hand sanitizer station use (606—yes), the method 600 continues at block 608.

At block 608, the activation module 428 determines whether the user associated with the matched facial data has reached a safe use limitation. If the activation module 428 determines that the user associated with the matched facial data has reached a safe use limitation (608—yes), the method 600 ends and the UV light source is not activated. If the activation module 428 determines that the user associated with the matched facial data has not reached a safe use limitation (608—no), the method 600 continues at block 610 and the activation module 428 activates the UV light source. At block 612, the exposure tracking module 426 updates exposure data for the user based on the exposure resulting from the activation of the UV light source at block 610 and the method ends.

FIG. 7 is a flowchart of another example method for enforcing a safe use standard/exposure limit for a UV hand sanitizer based on facial recognition according to another embodiment. The illustrated method 700 begins at block 702. At block 702, the selectable content presentation module 520 displays a plurality of graphic elements associated with content the user may select from (e.g. advertisement ("ad") choices). At block 704, a determination as to whether the sensor 226 has detected the presence of hands or another object in the compartment 220. If not (704—No), the method 700 returns to step 702 and the presentation of the advertisement choices. It is determined that the sensor 226 has detected hands or an object in the compartment 220 (704—Yes), the exposure limiter 132 or a module thereof applies facial recognition algorithms to an image captured by the camera 214 at block 706. The intent of this analysis in one embodiment is to identify facial features by extracting landmarks from the image of the user's face. Landmarks that are commonly used in facial recognition algorithms include the relative position, size, and shape of the eyes, nose, cheekbones, and jaw. This data is then compared with stored facial data associated with previous usage of the hand sanitizer station 106 to see if this user has previously used the UV sanitizer station 106a (or any other UV sanitizer stations such as station 106n).

If the current user's facial features match a previous user in the facial data 248, the past usage associated with this previous user is obtained. At block 708, the activation module 428 compares this past usage history (occasionally referred to herein as exposure data or usage data) to the safe use standard to see if this current user would exceed this standard. If the current use is considered excessive, the method 700 does not activate UV sanitization and returns to displaying ad choices in step 702. In some embodiments, the UV sanitizer station 106 displays an error message on the display 210 informing the user that this usage would exceed their recommended maximum UV exposure.

In an alternative embodiment, the UV sanitizer station 100 does not store any facial data and usage data locally, but rather relies exclusively on live access to the facial data and usage data maintained by the server 122 (e.g. in the storage device 341). In one such embodiment, the UV sanitizer station 106 will transmit facial data (either the analyzed landmarks recovered from the camera image or the actual image acquired by the camera 214) to the server 122. The server 122 is then responsible for comparing the user's face against stored facial data in order to identify a user and a usage history (from exposure data). The server 122 can then either transmit the usage history back to the UV sanitizer station 106 for the block 708 analysis, or the server 708 can perform this analysis itself (by comparing the usage history/exposure data against the safe use standard). If the server 122 performs this analysis, the server would then send a "activate UV sanitization" or "don't activate UV sanitization" signal back to the UV sanitizer station 106. In one embodiment, whether or not the server 122 performs the block 708 analysis, the server 122 is responsible for storing the facial data and/or updated usage data in its storage device 341.

If the activation module 428 determines that the current usage does not exceed the safe usage standard for this user, the UV sanitizer station 106 activates the hand sanitizer at block 710 (by turning on the UV light source 222 and the blower 224) and the selected content presentation module 526 concurrently presents an advertisement or other content on the display 210 at step 712. Once the hand sanitizer process has completed and the advertisement has been displayed, at block 714, the selected content presentation module 526 of the UV sanitizer station 106 presents to the user a promotion that is related to the ad displayed at step 712.

At step 716, the exposure quantification module 430 of the UV sanitizer station 106 submits data to the server 122 concerning this usage of the station 106. In particular, the station 106 must identify that this particular user has used the UV sterilization process. If the user was identified as a previous user through facial recognition, depending on the embodiment, all that may be necessary is to submit the user identifier of that user and the date and time that the process was provided. In embodiments where facial data from multiple images of the same individual are stored in server 122 data storage device 341, the UV sanitizer station 106 submits the user identifier, facial data from the just captured image of the user, and the data and time of the process to the server 122.

In one embodiment, when communicating with the server 122, the UV sanitizer station 106 may also download user data and usage data (e.g. exposure data 248) from the server 122 in order to supplement the data 248 that the UV sanitizer station 106 maintains in its own memory 240. This takes place at block 718, and is one method of ensuring that UV sanitizer station 106a will be aware of uses at all other stations 106, including second UV sanitizer station 106b. However, it should be recognized that in some embodiments the UV sanitizer station 106 does not make use of local data 248 and instead relies upon the server 122 to maintain this data and block 718 is not necessary. The method 700 then ends.

FIG. 8 is a flowchart of an example method for touch-less user-selection of content for presentation on a hand sanitizer device 106 according to another embodiment. The illustrated method 800 begins at block 805. At block 805, the selectable content presentation module 520 presents a plurality of ad choices (e.g. graphic elements associated with content eligible for presentation to the user) on a display 210. At block 810, the selectable content presentation module 520 highlights the next add choice and pauses at block 815 (e.g. for 1-3 seconds).

At block 820, the selection determination module 522 determines whether an initiation event is detected (e.g. whether the sensor 226 has detected the presence of the user's hands or another object in the compartment 220). If the selection determination module 522 does not detect an initiation event (820—No), the method 800 continues to block 825. If the selection determination module 522 does detect an initiation event (820—Yes), the method 800 continues at blocks 835 and 840.

At block 825, the selectable content presentation module 520 determines whether it is time to change ads (e.g. to receive updated ads at the sanitizer station 106 from the server 122). If the selectable content presentation module 520 determines that it is not time to change ads (825—No), the method 800 continues at block 810 and the selectable content presentation module 520 highlights the next ad choice. If the selectable content presentation module 520 determines that it is time to change ads (825 Yes), the method continues at block 830 where the selectable content presentation module 520 receives new ads and promotions from the server 127 before continuing to block 805.

Blocks 835 and 840 occur concurrently. At block 835, the activation module 428 activates the hand sanitizer (e.g. by turning on the UV source). At block 840, the selected content presentation module 526 presents the currently highlighted ad choice. The method 800 continues at block 845. At block 845, the selected content presentation module 526 presents a promotion related to the ad displayed at block 840 (i.e. supplemental content). At block 850, the selection tracking module 524 reports the presentation of the promotion to the server 122. At block 855, the user redeems the promotion and, at block 860, the selection tracking module 524 tracks the redemption (e.g. updates promotion redemption data stored on the storage device 341 of the server 122), and the method 800 ends. In one embodiment, the functionality of the selection tracking module 524 and the reporting of the redemption may be accomplished by the retailer's point of sale system, a coupon redemption clearing house, an electronic coupon app provider or other system able to detect redemption of a particular coupon.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

Reference in the specification to "one embodiment" or "an embodiment" means that a particular feature, structure, or characteristic described in connection with the embodiment is included in at least one embodiment. The appearances of the phrase "in one embodiment" in various places in the specification are not necessarily all referring to the same embodiment.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Various implementations described herein may relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of an entirely hardware implementation, an entirely software implementation, or implementations containing both hardware and software elements. For instance, the technology may be implemented in software, which includes but is not limited to firmware, resident software, microcode, etc. Additionally, the disclosure is in no way limited to implementation in any specific programming language, or for any specific operating system or environment.

Furthermore, the technology can take the form of a computer program product accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), WebSocket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Accordingly, the disclosure is intended to be illustrative, but not limiting, of the scope of the subject matter set forth in the following claims.

What is claimed is:

1. A system comprising:
 a sensor configured to detect an initiation event;
 a camera configured to capture an image of a user's face responsive to the initiation event, the camera communicatively coupled to the sensor;
 an ultraviolet source configured to be activated responsive to facial recognition and a determination based on one of exposure data associated with the user and an absence thereof that the user has not exceed a safe use standard for ultraviolet light; the ultraviolet source activated for an activation duration that sanitizes a surface located within a compartment; and
 a display configured to visually present a plurality of graphic elements associated with a plurality of potential content for presentation to the user, the display communicatively coupled to the ultraviolet source and presenting user selected content to the user when the ultraviolet source is activated and responsive to determining a user's selection, wherein the user's selection is made touch-lessly.

2. The system of claim 1, wherein the content presented to the user has a duration similar to the activation duration.

3. The system of claim 1, wherein the display is further configured to present supplemental information to the user after a conclusion of the content presented to the user when the ultraviolet source is activated.

4. The system of claim 1, wherein the initiation event includes a presence of one or more of an object and a user's hand located within the compartment.

5. The system of claim 1, wherein the user's selection is determined responsive to the sensor detecting the initiation event.

6. The system of claim 1 further comprising:
 one or more micro-sonars configured to detect the user's movement in proximity to the display touch-lessly and communicatively coupled to the display to visually distinguish a graphic element associated with content based on the user's movements, the visually distinguished graphic element determined to be selected responsive to detecting the initiation event.

7. The system of claim 1 further comprising:
 the display configured to cycle through the potential content for presentation to the user while the ultraviolet source is activated and visually distinguish a different graphic element associated with potential content for presentation to the user while the ultraviolet source is activated at an interval, the visually distinguished graphic element determined to be selected responsive to detecting the initiation event.

8. The system of claim 1, wherein the ultraviolet source is configured to activate responsive to the user passing a screening and responsive to the facial recognition and determination based on one of the exposure data associated with the user and the absence thereof that the user has not exceed the safe use standard for ultraviolet light and remain inactive otherwise.

9. The system of claim 8, wherein the screening is based on one or more of a user's height and whether the user's facial features are determined to be similar to those of a child.

10. A method comprising:
   detecting, using a sensor, an initiation event;
   capturing, using a camera, an image of a user's face responsive to the initiation event;
   activating, responsive to facial recognition and a determination based on one of exposure data associated with the user and an absence thereof that the user has not exceed a safe use standard for ultraviolet light, an ultraviolet source; the ultraviolet source activated for an activation duration that sanitizes a surface located within a compartment;
   visually presenting, by a display, a plurality of graphic elements associated with a plurality of potential content for presentation to the user; and
   presenting user selected content to the user when the ultraviolet source is activated and responsive to determining a user's selection, wherein the user's selection is made touch-lessly.

11. The method of claim 10, wherein the content presented to the user has a duration similar to the activation duration.

12. The method of claim 10 further comprising:
   presenting supplemental information to the user after a conclusion of the content presented to the user when the ultraviolet source is activated.

13. The method of claim 10, wherein the initiation event includes a presence of one or more of an object and a user's hand located within the compartment.

14. The method of claim 10, wherein the user's selection is determined responsive to the sensor detecting the initiation event.

15. The method of claim 10 further comprising:
   detecting, by one or more micro-sonars, the user's movement in proximity to the display touch-lessly; and
   visually distinguishing a graphic element associated with content based on the user's movements, the visually distinguished graphic element determined to be selected responsive to detecting the initiation event.

16. The method of claim 10 further comprising:
   cycling through the potential content for presentation to the user while the ultraviolet source is activated and visually distinguishing a different graphic element associated with potential content for presentation to the user while the ultraviolet source is activated at an interval, the visually distinguished graphic element determined to be selected responsive to detecting the initiation event.

17. The method of claim 10, wherein the ultraviolet source is activated responsive to the user passing a screening and responsive to the facial recognition and determination based on one of the exposure data associated with the user and the absence thereof that the user has not exceed the safe use standard for ultraviolet light and the ultraviolet source remains inactive otherwise.

18. The method of claim 17, wherein the screening is based on one or more of a user's height and whether the user's facial features are determined to be similar to those of a child.

* * * * *